(12) United States Patent
Vo et al.

(10) Patent No.: US 6,727,229 B2
(45) Date of Patent: Apr. 27, 2004

(54) 11,12-SUBSTITUTED LACTONE KETOLIDE DERIVATIVES HAVING ANTIBACTERIAL ACTIVITY

(75) Inventors: Nha Huu Vo, Malden, MA (US); Ly Tam Phan, Malden, MA (US); Ying Hou, Everett, MA (US); Tongzhu Liu, Auburndale, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/223,144

(22) Filed: Aug. 19, 2002

(65) Prior Publication Data

US 2004/0038915 A1 Feb. 26, 2004

(51) Int. Cl.$^7$ .................. A01N 43/04; A61K 31/70; C07H 17/08
(52) U.S. Cl. ................. 514/29; 536/7.2; 536/7.3; 536/7.4
(58) Field of Search ............................ 514/29; 536/7.2, 536/7.3, 7.4

(56) References Cited

U.S. PATENT DOCUMENTS

| | | | |
|---|---|---|---|
| 6,124,269 A | | 9/2000 | Phan et al. |
| 6,399,582 B1 | * | 6/2002 | Hlasta et al. |
| 2003/0212011 A1 | * | 11/2003 | Guerry et al. ............... 514/29 |

FOREIGN PATENT DOCUMENTS

| | | |
|---|---|---|
| WO | WO 02/16380 A | 2/2002 |
| WO | WO 02/50091 A | 5/2002 |
| WO | WO 02/50092 A | 5/2002 |
| WO | PCT WO 03/024986 A1 | 3/2003 |

* cited by examiner

Primary Examiner—James O. Wilson
Assistant Examiner—Traviss C. McIntosh, III
(74) Attorney, Agent, or Firm—Jason D. Ferrone; Gaetano D. Maccarone

(57) ABSTRACT

Novel 11–12 substituted lactone ketolide derivatives and pharmaceutically-acceptable compositions comprising a therapeutically effective amount of a compound of the invention in combination with a pharmaceutically-acceptable carrier are described. Also described are a method for treating bacterial infections by administering to an animal a pharmaceutical composition containing a therapeutically effective amount of a compound of the invention and processes for the preparation of such compounds.

7 Claims, No Drawings

11,12-SUBSTITUTED LACTONE KETOLIDE DERIVATIVES HAVING ANTIBACTERIAL ACTIVITY

TECHNICAL FIELD

The present invention relates to novel macrolides having antibacterial activity and useful in the treatment and prevention of bacterial infections. More particularly, the invention relates to novel 11,12-lactone ketolides, 14-membered macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic families (14-, 15- and 16-membered ring derivatives) exhibit a wide range of characteristics (antibacterial spectrum, side-effects and bioavailability). Among the commonly used macrolides are erythromycin, clarithromycin and azithromycin.

Erythromycins A through D, represented by formula (E) as illustrated below,

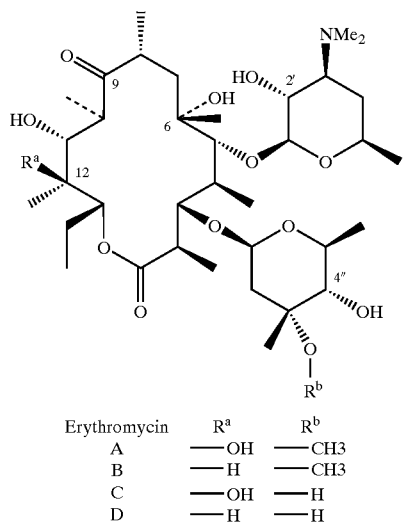

(E)

| Erythromycin | $R^a$ | $R^b$ |
|---|---|---|
| A | —OH | —CH3 |
| B | —H | —CH3 |
| C | —OH | —H |
| D | —H | —H | are well-known and potent antibacterial agents and are used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

EP 559896 of Kashimura et al, published Nov. 11, 1991, discloses 6-O-methylerythromycin derivatives having a tricyclic basic nuclear structure. Also, International Application WO 93/21200, published Apr. 22, 1992, of Asaka et al. discloses 5-O-desoaminylerythronolide derivatives containing a tricyclic carbamate structure.

Recently erythromycin derivatives containing a variety of substituents at the 6-O position have been disclosed in U.S. Pat. Nos. 5,866,549 and 6,075,011 as well as published International Application WO 00/78773. Furthermore, Ma et. al. have described erythromycin derivatives with aryl groups tethered to the C-6 position in *J. Med Chem.*, 44, pp 4137–4156 (2001).

International Application WO 02/16380 of Angehrn et al, discloses 14-membered macrolides as do published International Applications WO 02/50091 and WO 02/50092. Also, U.S. Pat. No. 6,124,269 discloses 2-halo-6-O-substituted ketolide; derivatives

SUMMARY OF THE INVENTION

The present invention provides a novel class 2-substituted 14-membered macrolide compounds possessing antibacterial activity toward Gram positive and Gram negative bacteria as well as macrolide resistant Gram positives. The compounds of the present invention are represented by the general formula I as illustrated below

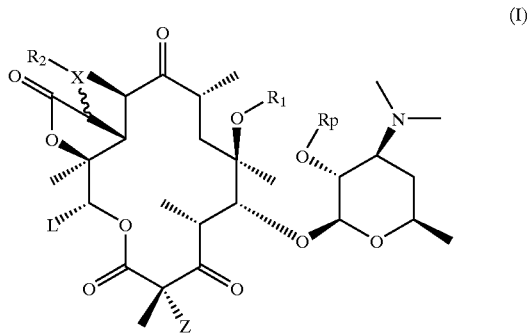

(I)

as well as the pharmaceutically acceptable salts, esters or prodrugs thereof.

In formula I above:

L is selected from the group consisting of:
(1) —CH(OH)CH$_3$;
(2) C$_1$–C$_6$ alkyl, optionally substituted with one or more substituents selected from the group consisting of aryl, substituted aryl, heteroaryl and substituted heteroaryl;
(3) C$_2$–C$_6$ alkenyl, optionally substituted with one or more substituents selected from the group consisting of aryl, substituted aryl, heteroaryl and substituted heteroaryl; and
(4) C$_2$–C$_6$ alkynyl, optionally substituted with one or more substituents selected from the group consisting of aryl, substituted aryl, heteroaryl and substituted heteroaryl;

R$_1$ is selected from the group consisting of C$_1$–C$_6$-alkyl, C$_2$–C$_6$-alkenyl and C$_2$–C$_6$-alkynyl, each optionally substituted with one or more substituents selected from the group consisting of:
(1) halogen;
(2) aryl;
(3) substituted aryl;
(4) heteroaryl;
(5) substituted heteroaryl;

(6) —O—$R_5$, where $R_5$ is selected from the group consisting of:
   a. hydrogen;
   b. aryl;
   c. substituted aryl;
   d. heteroaryl; and
   e. substituted heteroaryl;
(7) —O—$C_1$–$C_6$-alkyl-$R_5$, where $R_5$ is as previously defined;
(8) —O—$C_2$–$C_6$-alkenyl-$R_5$, where $R_5$ is as previously defined;
(9) —O—$C_2$–$C_6$-alkynyl-$R_5$, where $R_5$ is as previously defined; and
(10) —$N_6R_7$, where $R_6$ and $R_7$ are each independently selected from the group consisting of: hydrogen; $C_1$–$C_6$-alkyl, optionally substituted with one or more substituents selected from the group consisting of halogen, aryl, substituted aryl, heterocyclic and substituted heterocyclic; $C_2$–$C_6$-alkenyl, optionally substituted with one or more substituents selected from the group consisting of halogen, aryl, substituted aryl, heterocyclic and substituted heterocyclic; and $C_2$–$C_6$-alkynyl, optionally substituted with one or more substituents selected from the group consisting of halogen, aryl, substituted aryl, heterocyclic:and substituted heterocyclic; or $R_6R_7$ taken together with the nitrogen atom to which they are attached form a 3- to 7-membered ring which may optionally contain one or more hetero functions selected from the group consisting of —O—, —NH—, —N($C_1$–$C_6$-alkyl)—, —N(aryl)-, —N(heteroaryl)-, —S—, —S(O)— and —S(O)$_2$—;

$R_2$ is selected from the group consisting of:
  (1) hydrogen;
  (2) $C_1$–$C_6$-alkyl, optionally substituted with one or more substituents selected from the group consisting of:
    a. halogen;
    b. aryl;
    c. substituted aryl;
    d. heterocyclic;
    e. substituted heterocyclic;
    f. —O—$R_3$, where $R_3$ is selected from the group consisting of:
      i. hydrogen;
      ii. aryl;
      iii. substituted aryl;
      iv. heteroaryl; and
      v. substituted heteroaryl;
    g. —O—$C_1$–$C_6$-alkyl-$R_3$, where $R_3$ is as previously defined;
    h. —O—$C_2$–$C_6$-alkenyl-$R_3$, where $R_3$ is as previously defined;
    i. —O—$C_2$–$C_6$-alkynyl-$R_3$, where $R_3$ is as previously defined; and
    j. —$NR_6R_7$, where $R_6$ and $R_7$ are as previously defined;
  (3) $C_2$–$C_6$-alkenyl, optionally substituted with one or more substituents selected from the group consisting of:
    a. halogen;
    b. aryl;
    c. substituted aryl;
    d. heterocyclic;
    e. substituted heterocyclic;
    f. —O—$R_3$, where $R_3$ is as previously defined;
    g. —O—$C_1$–$C_6$-alkyl-$R_3$, where $R_3$ is as previously defined;
    h. —O—$C_2$–$C_6$-alkenyl-$R_3$, where $R_3$ is as previously defined;
    i. —O—$C_2$–$C_6$-alkynyl-$R_3$, where $R_3$ is as previously defined; and
    j. —$NR_6R_7$, where $R_6$ and $R_7$ are as previously defined; and
  (4) $C_2$–$C_6$-alkynyl, optionally substituted with one or more substituents selected from the group consisting of:
    a. halogen;
    b. aryl;
    c. substituted aryl;
    d. heterocyclic;
    e. substituted heterocyclic;
    f. —O—$R_3$, where $R_3$ is as previously defined;
    g. —O—$C_1$–$C_6$-alkyl-$R_3$, where $R_3$ is as previously defined;
    h. —O—$C_2$–$C_6$-alkenyl-$R_3$, where $R_3$ is as previously defined;
    i. —O—$C_2$–$C_6$-alkynyl-$R_3$, where $R_3$ is as previously defined; and
    j. —$NR_6R_7$, where $R_6$ and $R_7$ are as previously defined;

X is selected from the group consisting of:
  (1) S(O)n, where n is 0, 1, or 2; and
  (2) O;

Z is selected from the group consisting of:
  (1) hydrogen;
  (2) halogen; and
  (3) methyl;

provided that when X is S(O)n, $R_1$ is not methyl, and Rp is hydrogen or a hydroxy protecting group.

In another aspect of the present invention there are disclosed pharmaceutical compositions comprising a therapeutically effective amount of a compound of the invention in combination with a pharmaceutically acceptable carrier and treatment of bacterial infections with such compositions. Suitable carriers and methods of formulation are also disclosed. The compounds and compositions of the present invention have antibacterial activity.

In a further aspect of the present invention there are provided processes for the preparation of bicyclic macrolide derivatives of formula I wherein L, Z, X, $R_1$, $R_2$ and Rp are as previously described.

DETAILED DESCRIPTION OF THE INVENTION

A first embodiment of the present invention includes compounds represented by formula I, as illustrated above, as well as the pharmaceutically acceptable salts, esters and prodrugs thereof.

A preferred group of compounds of the present invention are those represented by formula I wherein, L is ethyl, X is sulfur, Z is fluorine, $R_1$ is methyl and where $R_2$ and Rp are as previously defined.

Particularly preferred compounds according to the invention are those wherein $R_2$ is selected from the group consisting of —$CH_2CH_2$—Ar where Ar is selected from the group consisting of:

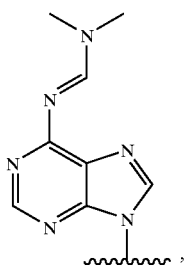 A1

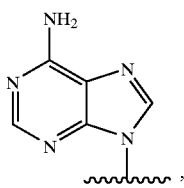 A2

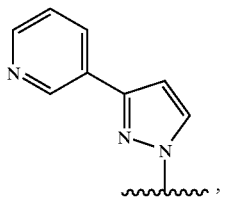 A3

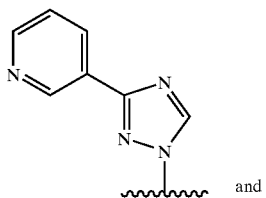 A4 and

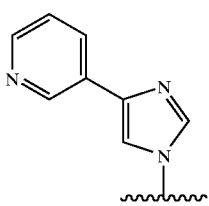 A5 and L, X, Z, $R_1$ and Rp are as previously described.

Representative compounds of the invention are those selected from the group consisting of:

Compound of formula I: L=$CH_2CH_3$, X=S, Z=F, $R_1$=$CH_3$, $R_2$=—$CH_2CH_2$-A1 and Rp=H;

Compound of formula I: L=$CH_2CH_3$, X=S, Z=F, $R_1$=$CH_3$, $R_2$=—$CH_2CH_2$-A2 and Rp=H;

Compound of formula I: L=$CH_2CH_3$, X=S, Z=F, $R_1$=$CH_3$, $R_2$=—$CH_2CH_2$-A3 and Rp=H;

Compound of formula I: L=$CH_2CH_3$, X=S, Z=F, $R_1$=$CH_3$, $R_2$=—$CH_2CH_2$-A4 and Rp=H;

Compound of formula I: L=$CH_2CH_3$, X=S, Z=F, $R_1$=$CH_3$, $R_2$=—$CH_2CH_2$-A5 and Rp=H;

Compound of formula I: L=$CH_2CH_3$, X=O, Z=F, $R_1$=$CH_3$, $R_2$=—$CH_2CH_2$-phenyl and Rp=H;

Compound of formula I: L=$CH_2CH_3$, X=S, Z=H, $R_1$=—$CH_2CHCH_2$, $R_2$=$CH_3$ and Rp=H;

Compound of formula I: L=$CH_2CH_3$, X=S, Z=F, $R_1$=—$CH_2CHCH_2$, $R_2$=$CH_3$ and Rp=H;

Compound of formula I: L=$CH_2CH_3$, X=S; Z=H, $R_1$=—$CH_2CHCH_2$-3-quinolyl, $R_2$=$CH_3$ and Rp=H; and Compound of formula I: L=$CH_2CH_3$, X=S, Z=F, $R_1$=—$CH_2CHCH_2$-3-quinolyl, $R_2$=$CH_3$ and Rp=H.

Definitions

The terms "$C_1$–$C_3$ alkyl," "$C_1$–$C_6$ alkyl" or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, ethyl, propyl, isopropyl, n-hexyl, octyl, decyl, dodecyl radicals.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The terms "$C_2$–$C_{12}$ alkynyl" or "$C_2$–$C_6$ alkynyl;" as used herein, denote a monovalent group derived from a hydrocarbon moiety containing from two to twelve or two to six carbon atoms having at least one carbon-carbon triple bond by the removal of two hydrogen atoms. Representative alkynyl groups include, but are not limited to for example, ethynyl, 1-propynyl, 1-butynyl, and the like.

The terms "halo" and "halogen," as used herein, refer to an atom selected from fluorine, chlorine, bromine and iodine.

The term "haloalkyl" denotes an alkyl group, as defined above, having one, two or three halogen atoms attached thereto and is exemplified by such groups as chloromethyl, bromoethyl, trifluoromethyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like. Aryl groups (including bicyclic aryl groups) can be unsubstituted or substituted with one, two or three substituents independently selected from lower alkyl, substituted lower alkyl, haloalkyl, alkoxy, thioalkoxy, amino, alkylamino, dialkylamino, acylamino, cyano, hydroxy, halo, mercapto, nitro, carboxaldehyde, carboxyl, alkoxycarbonyl and carboxamide. In addition, substituted aryl groups include tetrafluorophenyl and pentafluorophenyl.

The term "substituted aryl," as used herein, refers to an aryl group, as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, enzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "$C_3$–$C_{12}$-cycloalkyl" denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "heterocycloalkyl," as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "alkylamino" refers to a group having the structure —$NH(C_1$–$C_{12}$ alkyl) where $C_1$–$C_{12}$ alkyl is as previously defined.

The term "dialkylamino" refers to a group having the structure —$N(C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e. an alkoxy group, attached o the parent molecular moiety through a carbonyl group such as methoxycarbonyl, thoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —$C(O)NH(C_1$–$C_{12}$ alkyl) or —$C(O)N(C_1$–$C_{12}$ alkyl)($C_1$–$C_{12}$ alkyl).

"Hydroxy protecting group," as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-dimethylsilyl, tert-butyldiphenylsilyl, acyl substituted with an aromatic group and the like.

The term "protected hydroxy" refers to a hydroxy group protected with a hydroxy protecting group, as defined above, including benzoyl, acetyl, trimethylsilyl, triethylsilyl, methoxymethyl groups, for example.

"Amino protecting group," as used herein, refers to an easily removable group to which are known in the art to protect an amino group against undesirable reaction during synthetic procedures and to be selectively removable. The use of amino-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 3rd edition, John Wiley & Sons, New York (1999). Examples of amino protecting groups include, but are not limited to, 9-fluorenylmethyl carbamate, benzyl carbonate, tert-butyl carbonate, benzyl, p-toluene sulfonyl, acyl and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisoniers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al: describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts; and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. The term "prodrug" refers to compounds that are rapidly transformed in vivo to yield the parent compound of the above formula, for example by hydrolysis in blood. A thorough discussions is provided in T. Higuchi and V. Stella, "Pro-drugs as Novel Delivery Systems, Vol. 14 of the ACS Symposium Series, and in Edward B. Roche, ed., "Bioreversible Carriers in Drug Design", American Pharmaceutical Association and Pergamon Press, 1987, both of which are incorporated herein by reference.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then spotted to sterile 96-well microtiter plates. The inoculum for each bacterial strain was adjusted to $5.5 \times 10^5$ CFU/ml in appropriate MIC medium; 200 $\mu$l/well of this inoculum was added to the 96-well microtiter plate resulting in a final concentration of $1 \times 10^5$ CFU/ml. The 96 well plates were covered and incubated in a humidified atmosphere at 35+/−2° C. for 16–24 hours depending on the bacterial strain tested. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 µg/ml to about 0.03 µg/ml.

All in vitro testing follows the guidelines described in the Approved Standards M7-A5 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylfornamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethyl cellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from 0.01 to about 50 mg/kg body weight or more usually from 0.1 to about 25 mg/kg body weight. Single dose compositions may contain such amounts or submultiples thereof to make up the daily dose. In general, treatment regimens according to the present invention comprise administration to a patient in need of such treatment of from about 10 mg to about 1000 mg of the compound(s) of this invention per day in single or multiple doses.

The pharmaceutical compositions of this invention can be administered to fish by blending them in the fish feed to be administered orally or may be dissolved in water in which sick fish are placed to swim around (a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending on the age, body weight, condition of disease, etc. of the fish.

Abbreviations

Abbreviations which may be used in the descriptions of the schemes and the examples that follow are: Ac for acetyl; AIBN for azobisisobutyronitrile; Bn for benzyl; Boc for t-butoxycarbonyl; $Bu_3SnH$ for tributyltin hydride; Bz for benzoyl; CDI for carbonyldiimidazole; DBU for 1,8-diazabicyclo[5.4.0]undec-7-ene; DCC for 1,3-dicyclohexylcarbodiimide; DEAD for diethylazodicarboxylate; DIC for 1,3-diisopropylcarbodiimide; DMAP for dimethylaininopyridine; DMF for dimethyl formamide; DPPA for diphenylphosphoryl azide; EtOAc for ethyl acetate; KHMDS for potassium bis (trimethylsilyl) amide; LDA for lithium diisopropyl amide; MeOH for methanol; $Me_2S$ for dimethyl sulfide; MOM for methoxymethyl; NaN$(TMS)_2$ for sodium bis(trimethylsilyl)amide; NCS for N-chlorosuccinimide; NMO for 4-methylmorpholine N-oxide; PCC for pyridinium chlorochromate; PDC for pyridinium dichromate; Ph for phenyl; TEA for triethylamine; THF for tetrahydrofuran; TPP or $PPh_3$ for triphenylphosphine; TBS for tert-butyl dimethylsilyl; TMS for trimethylsilyl.

Synthetic Methods

The compounds and processes of the present invention will be better understood in connection with the following synthetic schemes which are illustrative of the methods by which the compounds of the invention may be prepared. The groups L, X, Z, $R_1$, $R_2$, and Rp are as defined previously unless otherwise noted below.

Scheme 1

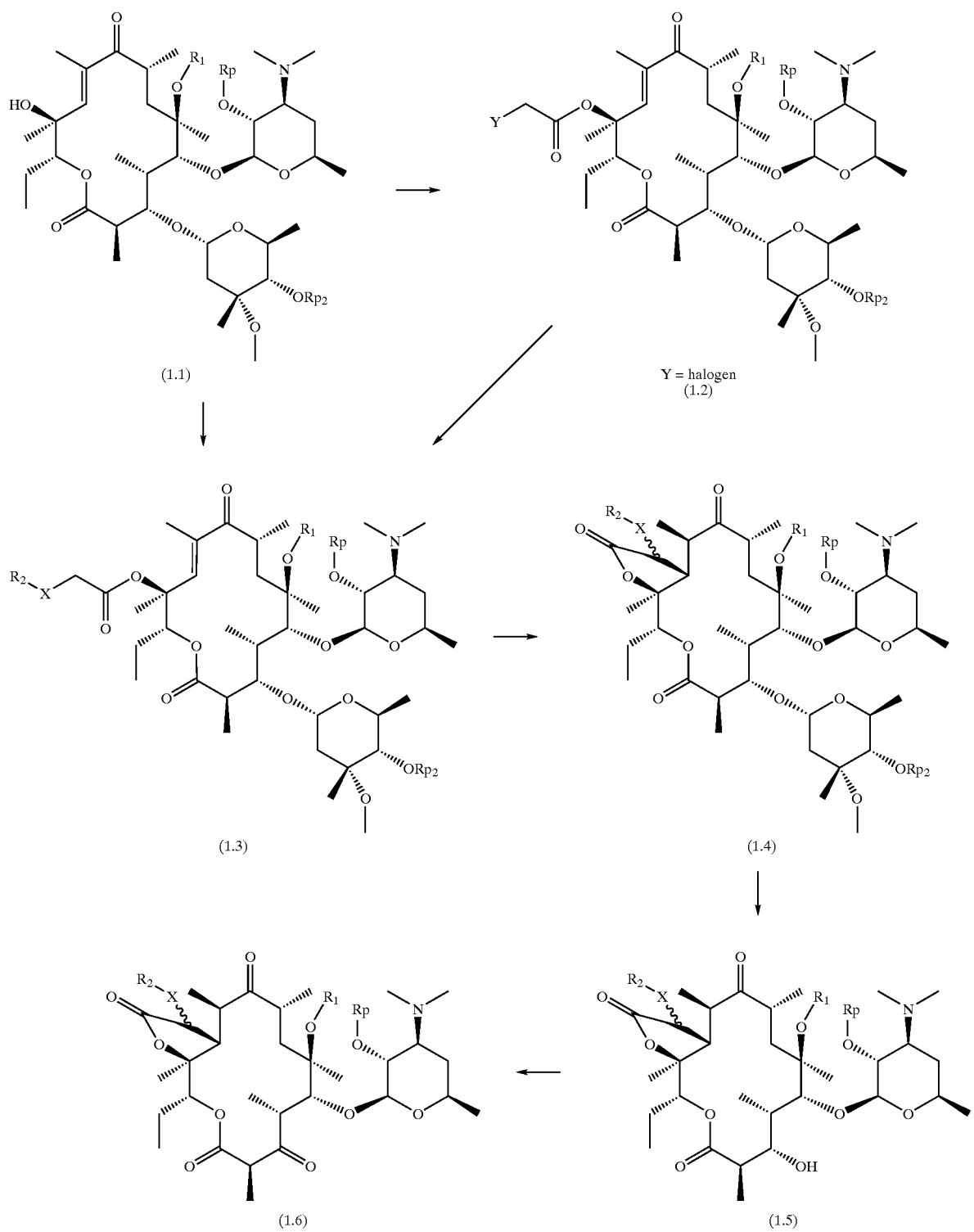

Scheme 1 illustrates the processes for the synthesis of compounds of formula (1.6) which serve as preferred intermediates for the preparation of the compounds of formula I. The compounds of the present invention can be prepared by methods which are well known in the art by modification of the readily available compounds of formula (1.1) which can be prepared according to the processes described by Baker et al. *J. Org. Chem.* 1988, 53, 2340–2345; Elliott et al. *J. Med. Chem.* 1988, 41, 1651–1659; Ma et al. *J. Med. Chem.* 2001, 44, 4137–4156, and Or et al. U.S. Pat. No. 6,075,011-B1. Compounds of formula (1.1) are reacted with an acylating reagent to provide compounds of formulas (1.2) and (1.3). Typical acylating conditions include reacting compounds of formula (1.1) with an acid anhydride, a mixed anhydride, an acid halide, a carboxylic acid and the like, optionally in the presence of a catalyst such as DMAP, DDC, DIC or the like, and optionally in the presence of a base such as sodium hydride, potassium tert-butoxide, LDA, KHMDS or the like, in an aprotic solvent such as dichloromethane, chloroform, tetrahydrofuran, N-methylpyrrolidinone, dimethylsulfoxide, N, N-dimethylformamide, N,N-dimethylacetamide, hexamethylphosphoric triamide or the like or a mixture thereof at a temperature of from −20° C. to 50° C. for 2–48 hours. A preferred acylating condition is reacting compounds of formula (1.1) with a carboxylic acid, DIC, or DMAP in dichloromethane at from 0° C. to room temperature. Compounds of formula (1.2), where Y is halogen or another activating group such as mesylate, tosylate or the like, can be converted to compounds of formula (1.3) by reacting with the anion of $R_2$—X—M where $R_2$ and X are previously defined and M is sodium, potassium, lithium or the like, or $R_2$—X—H in the presence of a base such as sodium hydride, potassium carbonate, LDA, sodium carbonate, or the likein the presence of an aprotic solvent such as tetrahydroiran, N-methylpyrrolidinone, dimethylsulfoxide, N,N-dimethylformamide, N,N-dimethylacetamide, hexamethylphosphoric triamide or the like, or a mixture thereof, at a temperature of from −20° C. to 50° C. for 1–48 hours. Compounds of formula (1.3) undergo an intramolecular cyclization to provide compounds of formula (1.4) upon treatment with a base such as sodium hydride, potassium tert-butoxide, LDA, KHMDS or the like in an aprotic solvent such as tetrahydrofuran; N-methylpyrrolidinone, dimethylsulfoxide, N,N-dimethylformamide or the like, or a mixture thereof, at a temperature of from −20° C. to 50° C. for 1–24 hours. The cladinose sugar of the compounds of formula (1.4) is removed by acid hydrolysis upon treatment with dilute hydrochloric acid, sulftric acid, nitric acid, trifluoroacidic acid or the like in an organic solvent such as methanol, ethanol, acetone, water, or the like, or a mixture thereof, at from room temperature to 80° C. for 2–48 hours to provide compounds of formula (1.5). Compounds of formula (1.6) are prepared by oxidation of the secondary alcohol of compounds of formula (1.5) using an oxidizing agent. Typical suitable oxidizing agents include, but are not limited to, 1,1,1-triacetoxy-1,1-dihydro-1,2-benziodoxol-3(1H)-one ("Dess-Martin reagent"), $NCS/Me_2S$, TPAP/NMO, PCC, PDC, sulfur trioxide pyridine complex in DMSO, or oxalyl chloride in DMSO, and the like (see, J. March, *Advanced Organic Chemistry* $4^{th}$ ed., Wiley & Son, Inc., 1992, and the references therein) in an aprotic solvent such as methylene chloride, ethylene chloride, THF, chloroform, DMF, acetonitrile or the like at a temperature from about −20° C. to 50° C. for about 1 to 48 hours.

Scheme 2

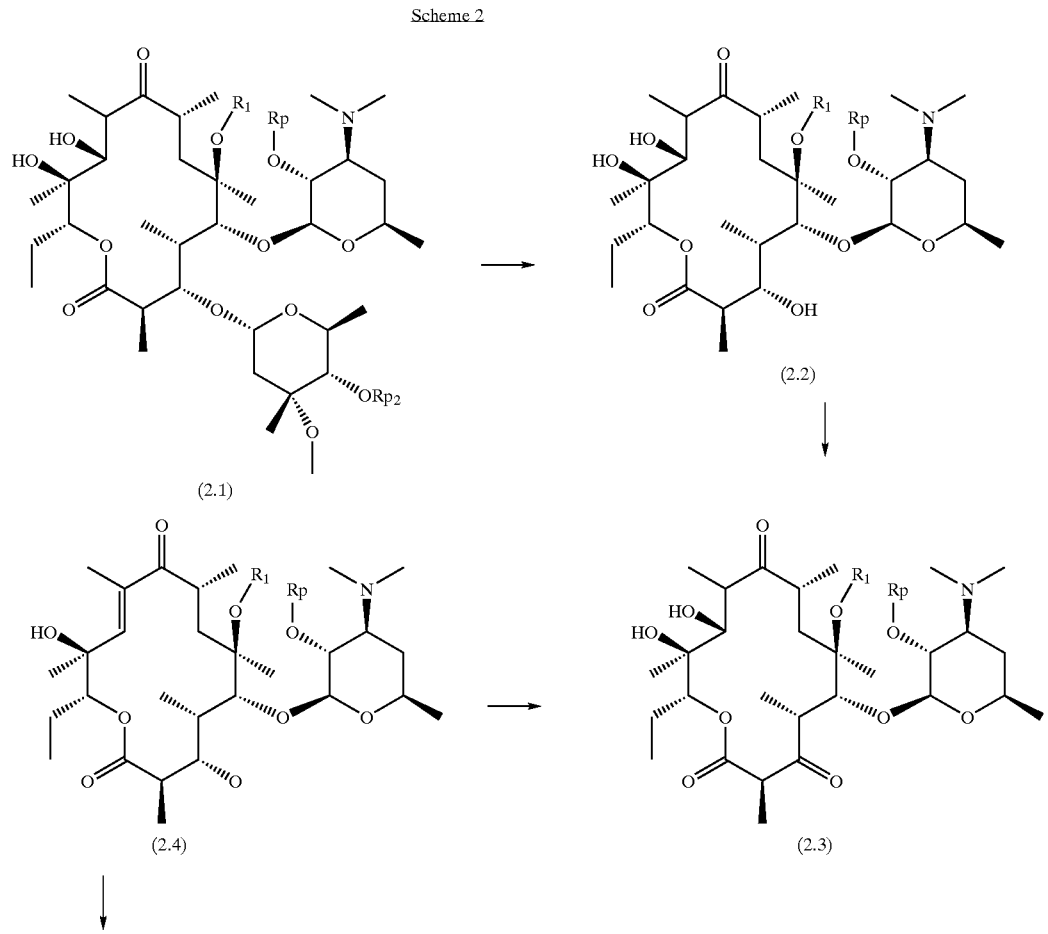

-continued

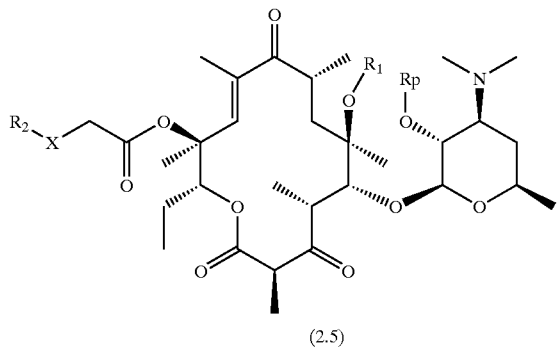
(2.5)

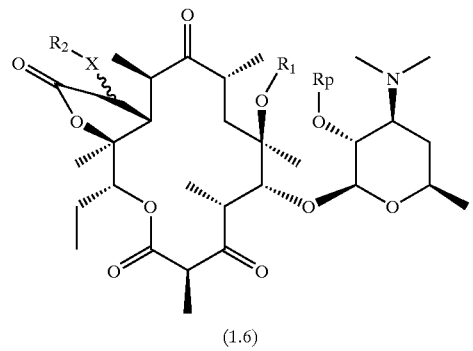
(1.6)

Another process for the preparation of intermediates of formula (1.6) involves hydrolyzing compounds of formula (2.1) (repared according to Ma et al. *J. Med. Chem.* 2001, 44, 4137–4156 and Or et al. U.S. Pat. No. 6,075,011-B1) with dilute hydrochloric acid, sulfuric acid, nitric acid, trifluoroacidic acid or the like in an organic solvent such as methanol, ethanol, acetone, water or the like, or mixtures thereof, at from room temperature to 80° C. for 248 hours to provide compounds of formula (2.2). Compounds of formula (2.3) are prepared by oxidation of the secondary alcohol of compounds of formula (2.2) using an oxidizing agent. Ttypical suitable oxidizing agents include, but are not limited to, 1,1,1-triacetoxy-1,1-dihydro-1,2-benziodoxol-3 (1H)-one ("Dess-Martin reagent"), NCS/Me$_2$S, TPAP/NMO, PCC, PDC, sulfur trioxide pyridine complex in DMSO, or oxalyl chloride in DMSO, and the like (see, J. March, *Advanced Organic Chemistry* 4$^{th}$ ed., Wiley & Son, Inc., 1992, and the references cited therein) in an aprotic solvent such as methylene chloride, ethylene chloride, THF, chloroform, DMF, acetonitrile or the like at a temperature from about –20° C. to about 50° C. for about 1 to 48 hours. Compounds of formula (2.4) are prepared by reaction with a sulfonyl reagent such as methane sulfonic anhydride, methane sulfonyl chloride, toluene sulfonyl chloride and the like optionally in the presence of a base such as DMAP, pyridine, triethylamine, sodium hydride, LDA, or the like in an aprotic solvent such as dichloromethane, chloroform, tetrahydrofuran, N-methylpyrrolidinone, dimethylsulfoxide, N,N-dimethylformamide, pyridine, or the like, or mixtures thereof, at a temperature from –20° C. to 50° C. for 2–48 hours to provide the an activated sulfonyl intermediate which is further treated with DBU, potassium tert-butoxide, KHMDS, or the like in an organic solvent such as dichloromethane, tetrahydrofuran, N-methylpyrrolidinone, dimethylsulfoxide, N,N-dimethylformamide, N,N-dimethylacetamide, or the like at a temperature from –20° C. to 50° C. for 2–48 hours. Compounds of formula (2.5) are prepared by reacting compounds of formula (2.4) with an acid anhydride, a mixed anhydride, an acid halide, a carboxylic acid or the like, optionally in the presence of a catalyst such as DMAP, DDC, DIC or the like and optionally in the presence of a base such as sodium hydride, potassium tert-butoxide, LDA, KHMDS or the like in an aprotic solvents such as dichloromethane, chloroform, tetrahydrofuran, N-methylpyrrolidinone, dimethylsulfoxide, N,N-dimethylformamide, N,N-dimethylacetamide, hexamethylphosphoric triamide or the like, or mixtures thereof, at a temperature from –20° C. to 50° C. for 2–48 hours. A preferred acylating condition is reacting compounds (2.4) with a carboxylic acid, DIC, or DMAP in dichloromethane at from 0° C. to room temperature to provide compounds of formula (2.5). Compounds of formula (2.5) undergo an intramolecular cyclization to provide compounds of formula (1.6) upon treatment with a base such as sodium hydride, potassium tert-butoxide, LDA, KHMDS or the like in an aprotic solvent such as tetrahydrofuran, N-methylpyrrolidinone, dimethylsulfoxide, N,N-dimethylformamide or a mixture thereof or the like at a temperature from –20° C. to 50° C. for 1–24 hours.

Scheme 3

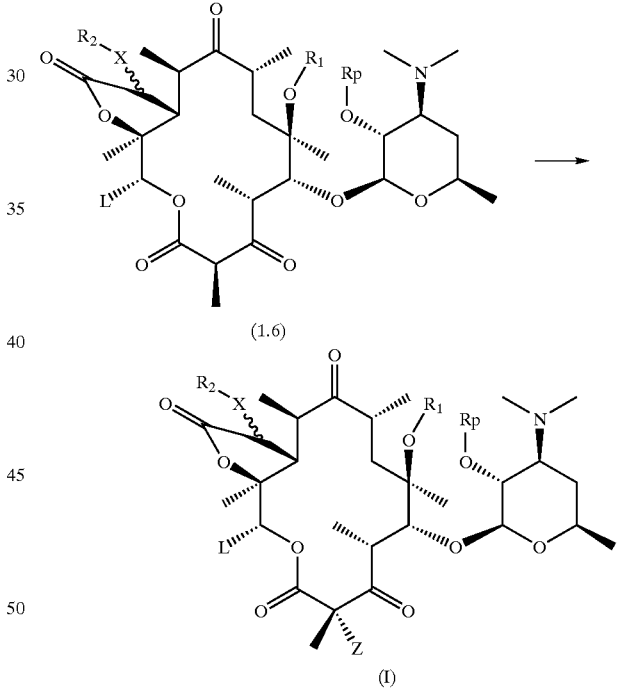

Scheme 3 illustrates the procedure by which compounds of formula (1.6) may be converted to compounds of formula I by treatment with a halogenating reagent by the process disclosed in U.S. Pat. No. 6,124,269 and International Patent WO 00/62783, which are hereby incorporated by reference herein in their entirety. The halogenating reagent acts to replace a hydrogen atom with a halogen atom at the C-2 position of the ketolide. Various halogenating reagents may be used for this procedure.

Suitable fluorinating reagents include, but are not limited to, N-fluorobenzenesulfornimide in the presence of base, 10% F$_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate and N-fluoroperfluoropiperidine in the presence of base.

Suitable chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, $Cl_2$, and NaOCl in the presence of acetic acid.

Suitable brominating reagents include, but are not limited to, $Br_2$.pyridine.HBr, $Br_2$/acetic acid, N-bromosuccinimide in the presence of base, $LDA/BrCH_2CH_2Br$, and LDA/$CBr_4$.

Suitable iodinating reagents, include but are not limited to, N-Iodosuccinimide in the presence of base and $I_2$.

Suitable bases for the halogenating reactions requiring them are compounds such as, for example, alkali metal hydrides such as NaH and KH, and amine bases such as LDA or triethylamine. As is well known in the art, different reagents may require a different type of base.

A preferred halogenating reagent is N-fluorobenzenesulfonimide in the presence of —sodium hydride.

Suitable solvents for use in the halogenating reactions are dimethylformamide, dimethyl sulfoxide, pyrrolidinone and the like.

Alternatively, the C-2 position of the compounds of formula 2.1 can be methylated by treatment with a methyl halide in the presence of a base such as $K_2CO_3$, NaOH, NaH, LDA or the like, with or without a phase transfer catalyst such as tetrabutylammonium iodide, or the like, in THF, methylene chloride, DMF, DMSO, water or the like, or combinations thereof, at from about 0° C. to about 50° C. for 1–24 hours to provide compounds of formula I. The Rp protecting group of the compounds of formula I can be removed upon treatment with methanol at from room temperature to 50° C.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula I: L—$CH_2CH_3$, Z=F, X=S, $R_1=CH_3$, $R_2$=—$CH_2CH_2$-A1 and Rp=H Step 1a. Compound of formula 2.1 of Scheme 2: $R_1=CH_3$, Rp $C(O)CH_3$ and $Rp_2=C(O)CH_3$;

Acetic anhydride (4.5 mL, 48 mmol) was added dropwise into a solution of clarithromycin (15 g, 20 mmol), triethylamine (7 mL), and DMAP (250 mg, 2.0 mmol) in $CH_2Cl_2$ (100 mL). The mixture was stirred at room temperature overnight and poured over water. The resulting aqueous solution was extracted with $CH_2Cl_2$. The combined extracts were dried ($K_2CO_3$), filtered and concentrated to give the crude title product as a solid foam (17.8 g).

MS (ESI) m/z=832 (M+H)$^+$.

Step 1b. Compound of formula 1.1 of Scheme 1: $R_1=CH_3$, Rp=$C(O)CH_3$ and $Rp_2=C(O)CH_3$;

A mixture of the crude compound from Step 1a (17.8 g), triethylamine (8 mL), and ethylene carbonate (80 g) was heated to 90° C. overnight. The mixture was cooled to room temperature, taken up in water, and extracted with $CH_2Cl_2$. The combined extracts were dried ($K_2CO_3$), filtered and concentrated under reduced pressure. The crude residue was purified on silica ($CH_2Cl_2$:2M $NH_3$/MeOH/98:2) to give the pure title compound as a tan solid (10.6 g).

MS (ESI).m/z=814 (M+H)$^+$.

Step 1c. Compound of formula 1.2 of Scheme 1: Y=Cl, $R_1=CH_3$, Rp=$C(O)CH_3$ and $Rp_2=C(O)CH_3$;

Into a mixture of the compound of Step 1b (1.79 g, 2.2 mmol), DMAP (0.54 g, 4.4 mmol) and chloroacetic acid (0.42 g, 4.4 mmol), in $CH_2Cl_2$ (10 mL) at 0° C., DIC (0.69 mL, 4.4 mmol) was added. The mixture was stirred at 0° C. for 6 hours. Additional DIC (0.35 mL, 2.2 mmol), DMAP (0.27 g, 2.2 mmol) and chloroacetic acid (0.21 g, 2.2 mmol) were added. The mixture was stirred at 4° C. overnight. The mixture was placed directly on silica gel column (eluted with $CH_2Cl_2$:2M $NH_3$/MeOH/97:3) to provide the title compound (1.5 g).

MS (ESI) m/z=890 (M+H)$^+$.

Step 1d. Compound of formula 1.3 of Scheme 1: X=S, $R_1=CH_3$, R2==—$CH_2CH_2$-A1, Rp=$C(O)CH_3$ and $Rp_2=C(O)CH_3$;

A degassed mixture of the compound from Step 1c (970 mg, 1.1 mmol), [6-amino-9H-purine]-1-ethanethiol (234 mg, 1.20 mmol), and NaI (10 mg) was taken up in acetone (30 mL). Into the mixture DBU (183 mg, 1.2 mmol) was added. The mixture was stirred under $N_2$ overnight. Acetone was removed under reduced pressure, the residue was taken up in a saturated aqueous solution of $NaHCO_3$ and extracted with $CHCl_3$. The combined extracts were dried ($Na_2SO_4$), filtered and concentrated under reduced pressure. The crude residue was purified on silica ($CH_2Cl_2$:2M $NH_3$ in MeOH, 95:5) to give the title compound (750 mg).

MS (ESI) m/z 1104 (M+H)$^+$.

Step 1e. Compound of formula 1.4 of Scheme 1: X=S, $R_1=CH_3$, R2==—$CH_2CH_2$-A1, Rp=$C(O)CH_3$, and $Rp_2=C(O)CH_3$;

Sodium hydride (120 mg of 60% pure compound, 3.00 mmol) was added to a solution of the compound of Step 1d (750 mg, 0.72 mmol) in DMF (10 mL) at 0° C. The reaction mixture was stirred at 0° C. for one hour, treated with a saturated aqueous solution of $NaHCO_3$ and extracted with ethyl acetate. The extract was washed with a saturated aqueous solution of $NaHCO_3$, and with brine, then dried ($Na_2SO_4$), filtered and concentrated under reduced pressure to provide the crude title compound (750 mg).

MS (ESI) m/z 1104 (M+H)$^+$.

Step 1f. Compound of formula 1.5 of Scheme 1: X=S, $R_1=CH_3$, $R_2$=—$CH_2CH_2$-A1 and Rp=$C(O)CH_3$;

To a solution of the crude compound of Step 1e (750 mg) in EtOH (10 mL), there was added 1N HCl (10 ml) at room temperature. The reaction mixture was stirred at room temperature overnight. Another portion of 1N HCl (10 ml) was added to the reaction mixture. The mixture was heated at 40° C. for three hours, cooled to room temperature, taken up in ethyl acetate, washed with a saturated aqueous solution of $NaHCO_3$, and with brine, then dried ($Na_2SO_4$), filtered and concentrated under reduced pressure. The crude product was purified by flash chromatography ($CH_2Cl_2$:2N $NH_3$/MeOH/95:5) to give 410 mg of the pure title compound.

MS (ESI) m/z=849 (M+H)$^+$.

Step 1g. Compound of formula 1.5 of Scheme 1: X=S, $R_1=R_2$=—$CH_2CH_2$-A1 and Rp=$C(O)CH_3$;

Sodium hydride (9.5 mg, 0.24 mmol) was added to a solution of the compound of Step 1f (50 mg, 0.059 mmol) in DMF (10 mL) at 0° C. The reaction mixture was stirred for 50 minutes at 0° C., treated with a saturated aqueous solution of NaHCO$_3$ and extracted with ethyl acetate. The organic layer was washed with a saturated aqueous solution of NaHCO$_3$, and with brine, then dried (Na$_2$SO$_4$), filtered and concentrated under reduced pressure to give the crude title compound (51 mg).

MS (ESI) m/z=904 (M+H)$^+$.

Step 1h. Compound of formula 1.6 of Scheme 1: X=S, R$_1$=CH$_3$, R$_2$=—CH$_2$CH$_2$-A1 and Rp=C(O)CH$_3$;

Dess-Martin reagent (3.5 mg, 0.083 mmol) was added to a solution of the compound of Step 1g (50 mg, 0.055 mmol) in CH$_2$Cl$_2$ (0.8 mL) at room temperature. The reaction mixture was stirred, at room temperature for one hour. The reaction was quenched by addition of a 10% aqueous solution of Na$_2$S$_2$O$_3$. The mixture was extracted with ethyl acetate. The combined extracts were washed with a saturated aqueous solution of NaHCO$_3$, and with brine, then dried (Na$_2$SO$_4$), filtered and concentrated under reduced pressure to give the crude title compound (50 mg).

MS (ESI) m/z=902 (M+H)$^+$.

Step 1i. Compound of formula I: L=CH$_2$CH$_3$, Z=F, X=S, R$_1$=CH$_3$, R$_2$=—CH$_2$CH$_2$-A1 and Rp=C(O)CH$_3$;

Sodium hydride (9 mg, 0.22 mmol) was added to a solution of the compound from Step 1h (50 mg, 0.055 mmol) in DMF (0.5 mL) at 0° C. The slurry was stirred for 30 minutes at 0° C., followed by the addition of N-fluorobenzenesulfonimide (17.5 mg, 0.055 mmol) to the reaction mixture at 0° C. The mixture was stirred at 0° C. for 10 minutes, then at room temperature for 20 minutes. A saturated aqueous solution of NaHCO$_3$ was added to the reaction mixture. The resulting solution was extracted with ethyl acetate. The combined extracts were washed with a saturated aqueous solution of NaHCO$_3$, and with brine, then dried (Na$_2$SO$_4$), filtered and concentrated under reduced pressure to give the crude title compound (45 mg).

MS (ESI) m/z=920 (M+H)$^+$.

Step 1j. Compound of formula I: L=CH$_2$CH$_3$, Z=F, X=S, R$_1$=CH$_3$, R$_2$=—CH$_2$CH$_2$-A1 and Rp=H.

The compound from Step 1i is treated with methanol at reflux temperature to provide the title compound.

Example 2

Compound of Formula I: L=CH$_2$CH$_3$, X=S, Z=F, R$_1$=CH$_3$, R$_2$=—CH$_2$CH$_2$-A2 and Rp=H Step 2a. Compound of formula I: L=CH$_2$CH$_3$, X=S, Z=F, R$_1$=CH$_3$, R$_2$=—CH$_2$CH$_2$-A2 and Rp=C(O)CH$_3$;

Into a solution of the crude compound from Step 1i (45 mg) in ethanol (2 mL) was added 1N HCl (2 ml). The mixture was stirred at 45° C. for 1 hour and 40 minutes and then concentrated under reduced pressure. The residue was treated with a saturated aqueous solution of NaHCO$_3$, and extracted with CHCl$_3$. The organic layer was washed with a saturated aqueous solution of NaHCO$_3$ and with brine, then dried (Na$_2$SO$_4$) filtered and concentrated under reduced pressure to give the crude title product (40 mg). The crude product was purified by flash chromatography (CH$_2$Cl$_2$:NH$_3$/MeOH/95:5) to give 11.5 mg of pure title compound.

MS (ESI) m/z=865 (M+H)$^+$.

Step 2b. Compound of formula I: L=CH$_2$CH$_3$, X=S, Z=F, R$_1$=CH$_3$, R$_2$=—CH$_2$CH$_2$-A2 and Rp=H;

A solution of the compound from Step 2a (11.5 mg) in methanol (2 mL) was stirred at room temperature overnight and concentrated under reduced pressure to give 11 mg of the title compound.

MS (ESI) m/z=823 (M+H)$^+$. $^{13}$C-NMR (125 MHz, CDCl$_3$): δ 217.7, d (202.9 and 202.6), 175.9, d (165.6 and 165.4), 155.3, 152.8, 149.8, 142.3, 119.8, 104.3, d (98.3 and 96.7), 87.3, 80.7, 79.8, 78.2, 70.4, 69.6, 65.8, 49.8, 47.4, 44.8, 41.8, 40.6, 40.2, 39.6, 39.2, 35.4, 32.3, 29.7, 28.1, d (25.5 and 25.4), 22.4, 21.2, 20.1, 17.9, 15.3, 15.1, 14.6, 10.6.

Example 3

Compound of Formula I: L=CH$_2$CH$_3$, X=S, Z=F, R$_1$=CH$_3$, R$_2$=—CH$_2$CH$_2$-A3 and Rp=H Step 3a. Compound of formula 1.3 of Scheme 1: X=S, R$_1$=CH$_3$, R$_2$=—CH$_2$CH$_2$-A3, Rp=C(O)CH$_3$ and Rp$_2$=C(O)CH$_3$;

The title compound is obtained according to the procedure described in Step 1d of Example 1 from the compound of Step 1d and [3-(3-pyridinyl)-1H-pyrazole]-1-ethanethiol (prepared as described in WO200216380-A1).

Step 3b. Compound of formula 1.4 of Scheme 1: X=S, R$_1$=CH$_3$, R$_2$=—CH$_2$CH$_2$-A3, Rp=C(O)CH$_3$ and Rp$_2$=C(O)CH$_3$;

The title compound is obtained from the compound of Step 3a according to the proceduredescribed in Step 1e of Example 1.

Step 3c. Compound of formula 1.5 of Scheme 1: X=S, R$_1$=CH$_3$, R$_2$=—CH$_2$CH$_2$-A3 and Rp=C(O)CH$_3$;

The title compound is obtained from the compound of Step 3b according to the procedure described in Step 1f of Example 1.

Step 3d. Compound of formula 1.6 of Scheme 1: X=S, R$_1$=CH$_3$, R$_2$=—CH$_2$CH$_2$-A3 and Rp=C(O)CH$_3$;

The title compound is obtained from the compound of Step 3c according to the procedure described in Step 1h of Example 1.

Step 3e. Compound of formula I: L=CH$_2$CH$_3$, X=S, Z=F, R$_1$=CH$_3$, R$_2$=—CH$_2$CH$_2$-A3 and Rp=C(O)CH$_3$;

The title compound is obtained from the compound of Step 3d according to the procedure described in Step 1i of Example 1.

Step 3f. Compound of formula I: L=CH$_2$CH$_3$, X=S, Z=F, R$_1$=CH$_3$, R$_2$=—CH$_2$CH$_2$-A3 and Rp=H.

The title compound is obtained from the compound of Step 3e according to the procedure described in Step 2b of Example 2.

Example 4

Compound of Formula I: L=CH$_2$CH$_3$, X=S, Z=F, R$_1$=CH$_3$, R$_2$=—CH$_2$CH$_2$-A4 and Rp=H.

Step 4a. Compound of formula 1.3 of Scheme 1: X=S, R$_1$=CH R$_2$=—CH$_2$CH$_2$-A4, Rp=C(O)CH$_3$ and Rp$_2$=C(O)CH$_3$;

The title compound is obtained from the compound of Step 1c of Example 1 and [3-(3-pyridinyl)-1H-1,2,4-triazole-1-yl]-ethanethiol (prepared as described in WO200216380-A1) according to the procedure described in Step 1d.

Step 4b. Compound of formula 1.4 of Scheme 1: X=S, R$_1$=CH$_3$, R$_2$=—CH$_2$CH$_2$-A4, Rp=C(O)CH$_3$ and Rp$_2$=C(O)CH$_3$;

The title compound is obtained from the compound of Step 4a according to the procedure described in Step 1e of Example 1.

Step 4c. Compound of formula 1.5 of Scheme 1: X=S, R$_1$=CH$_3$, R$_2$=—CH$_2$CH$_2$-A4 and Rp=C(O)CH$_3$;

The title compound is obtained from the compound of Step 4b according to the procedure described in Step 1f of Example 1.

Step 4d. Compound of formula 1.6 of Scheme 1: X=S, $R_1$=$CH_3$, $R_2$=—$CH_2CH_2$-A4 and Rp=C(O)$CH_3$;

The title compound is obtained from the compound of Step 4c according to the procedure described in Step 1h of Example 1.

Step 4e. Compound of formula I: L=$CH_2CH_3$, X=S, Z=F, $R_1$=$CH_3$, $R_2$=—$CH_2CH_2$-A4 and Rp=C(O)$CH_1$;

The title compound is obtained from the compound of Step 4d according to the procedure described in Step 1i of Example 1.

Step 4f. Compound of formula I: L=$CH_2CH_3$, X=S, Z=F, $R_2$=—$CH_2CH_2$-A4 and Rp=H.

The title compound is obtained from the compound of Step 4e according to the procedure described in Step 2b of Example 2.

Example 5

Compound of Formula I: L=$CH_2CH_3$, X=S, Z=F, $R_1$=$CH_3$, $R_2$=—$CH_2CH_2$-A5 and Rp=H Step 5a. Compound of formula 1.3 of Scheme 1: X=S, $R_1$=$CH_3$, $R_2$=—$CH_2CH_2$-A5, Rp=C(O)$CH_3$ and $Rp_2$=C(O)$CH_3$;

The title compound is obtained from the compound of Step 1c of Example 1 and [4-(3-pyridinyl)-1H-imidazole]-1-ethanethiol (prepared as described in WO200216380-A1) according to the proedure described in Step 1d of Example 1.

Step 5b. Compound of formula 1.4 of Scheme 1: X=S, $R_1$=$CH_3$, $R_2$=—$CH_2CH_2$-A5, Rp=C(O)$CH_3$ and $Rp_2$=C(O)$CH_3$;

The title compound is obtained from the compound of Step 5a according to the procedure described in Step 1e of Example 1.

Step 5c. Compound of formula 1.5 of Scheme 1: X=S, $R_1$=$CH_3$, $R_2$=—$CH_2CH_2$-A5 and Rp=C(O)$CH_3$;

The title compound is obtained from the compound of Step 5b according to the procedure described in Step 1f of Example 1.

Step 5d. Compound of formula 1.6 of Scheme 1: X=S, $R_1$=$CH_3$, $R_2$=—$CH_2CH_2$-A5 and Rp=C(O)$CH_3$;

The title compound is obtained from the compound of Step 5c according to the procedure described in Step 1h of Example 1.

Step 5e. Compound of formula I: L=$CH_2CH_3$, X=S, Z=F, $R_1$=$CH_3$, $R_2$=—$CH_2CH_2$-A5 and Rp=C(O)$CH_3$;

The title compound is obtained from the compound of Step 5d according to the procedure described in Step 1i of Example 1.

Step 5f. Compound of formula I: L=$CH_2CH_3$, X=S, Z=F, $R_1$=$CH_3$, $R_2$=—$CH_2CH_2$-A5 and Rp=H.

The title compound is obtained from the compound of Step 5e according to the procedure described in Step 2b of Example 2.

Example 6

Compound of Formula I: L=$CH_2CH_3$, X=O, Z=F, $R_1$=$CH_3$, $R_2$=—$CH_2CH_2$-phenyl and Rp=H Step 6a. Compound of formula 1.1 of Scheme 1: $R_1$=$CH_3$, Rp=Bz and $Rp_2$=Bz;

A solution of a compound of formula 1.1 of Scheme 1: $R_1$=$CH_3$, Rp=H and $Rp_2$=H: (95.91 g, 131.51 mmol) in methylene chloride (1 L) containing benzoyl anhydride (90%, 6626 g, 289.30 mmol), (prepared according to Elliott et al. *J. Med. Chem.* 1988, 41, 1651–1659), triethylamine (54.81 mL, 433.95 mmol) and DMAP (320 mg, 2.63 mol) was heated to reflux overnight. The resulting mixture was washed with saturated $NaHCO_3$ solution and brine, concentrated under reduced pressure and recrystalized in acetonitrile to give 77.30 g of the title compound as a white solid.

MS (ESI) m/z=938 $(M+H)^+$. $^{13}$C-NMR (125 MHz, $CDCl_3$): δ 207.6, 175.2, 166.2, 165.2, 141.2, 138.9, 133.4, 132.5, 130.8, 129.7, 128.4, 128.1, 100.6, 95.9, 80.0, 79.6, 78.9, 78.3, 78.0, 73.2, 72.9, 72.4, 67.7, 63.7, 63.4, 50.6, 49.7, 44.9, 40.9, 39.7, 38.5, 35.4, 31.8, 22.2, 21.7, 21.3, 21.2, 18.7, 18.3, 15.5, 13.7, 10.6, 9.8.

Step 6b. Compound of formula 1.3 of Scheme 1: X=O, $R_1$=$CH_3$, $R_2$=—$CH_2CH_2$-phenyl, Rp=Bz and $Rp_2$=Bz;

A solution of the compound of Step 6a (200 mg, 0.21 mmol) and phenethyloxyacetic acid (180 mg, 0.42 mmol) in methylene chloride (2 mL) was treated with diisopropyl carbodiimide (0.16 mL, 1.05 mmol) and DMAP (5 mg) at room temperature overnight. The resulting mixture was diluted with methylene chloride (8 mL), washed with saturated $NaHCO_3$ solution (×2) and brine, concentrated under reduced pressure and purified by silica gel chromatography (10% acetone in hexane) to afford 209 mg of the title compound as a white solid.

MS (ESI) m/z=1100 $(M+H)^+$. $^{13}$C-NMR (125 MHz, $CDCl_3$): δ 205.1, 174.3, 167.8, 166.2, 165.2, 139.8, 138.3, 137.4, 133.4, 132.5, 130.9, 129.8, 129.7, 129.6, 129.0, 128.9, 128.4, 128.1, 126.3, 100.7, 96.1, 94.0, 81.1, 80.4, 79.0, 78.3, 78.2, 75.5, 72.8, 72.6, 72.4, 67.7, 63.8, 63.4, 50.8, 49.7, 45.1, 42.0, 40.9, 39.1, 38.4, 36.1, 35.5, 31.6, 30.9, 23.5, 22.1, 21.2, 19.5, 18.4, 16.2, 13.1, 10.2.

Step 6c. Compound of formula 1.4 of Scheme 1: X=O, $R_1$=$CH_3$, $R_2$=—$CH_2CH_2$-phenyl, Rp=Bz and $Rp_2$=Bz;

The compound of step 6b is treated with potassium tert-butoxide in tetrahydrofuran at room temperature. The reaction mixture is quenched by saturated $NaHCO_3$ aqueous solution and extracted with ethyl acetate. The extracts are washed with water and brine, dried ($Na_2SO_4$), filtered and concentrated under reduced pressure to provide the crude title compound.

Step 6d. Compound of formula 1.5 of Scheme 1: X=O, $R_1$=$CH_3$, $R_2$=—$CH_2CH_2$-phenyl and Rp=Bz;

A solution of the title compound of Step 6c in 1N HCl-EtOH is heated at 40° C. for three hours. The reaction mixture is diluted with ethyl acetate, washed with a saturated aqueous solution of $NaHCO_3$ and with brine, then dried ($Na_2SO_4$), filtered and concentrated under reduced pressure to afford the title compound.

Step 6e. Compound of formula 1.6 of Scheme 1: X=O, $R_1$=$CH_3$, $R_2$=—$CH_2CH_2$-phenyl and Rp=Bz;

Dess-Martin reagent is added to a solution of the compound of Step 6d in $CH_2Cl_2$ at room temperature. The reaction mixture is stirred at room temperature for one hour. The reaction is quenched by addition of a 10% aqueous solution of $Na_2S_2O_3$. The mixture is extracted with ethyl acetate, the combined extracts washed with a saturated aqueous solution of $NaHCO_3$, and with brine, then dried ($Na_2SO_4$), filtered and concentrated under reduced pressure to give the crude title compound.

Step 6f. Compound of formula I: L=$CH_2CH_3$, X=O, Z=F, $R_1$=$CH_3$, $R_2$=—$CH_2CH_2$-phenyl and Rp=Bz;

Sodium hydride is added to a solution of the compound of Step 6e in DMF at 0° C. The slurry is stirred for 30 minutes at 0° C., followed by the addition of N-fluorobenzenesulfonimide at 0° C. The mixture is stirred at 0° C. for 10 minutes, then at room temperature for 20 minutes. A saturated aqueous solution of $NaHCO_3$ is added to the reaction mixture. The resulting solution is extracted with ethyl acetate. The combined extracts are washed with a saturated aqueous solution of $NaHCO_3$, and with brine, then dried ($Na_2SO_4$), filtered and concentrated under reduced pressure to give the crude title compound.

Step 6g. Compound of formula I: L=$CH_2CH_3$, X=O, Z=F, $R_1$=$CH_3$, $R_2$=—$CH_2CH_2$-phenyl and Rp=H.

A solution of the compound from Step 6h in methanol is heated to reflux overnight. The resulting solution is concentrated under reduced pressure and purified by silica gel chromatography to give the title compound.

Example 7

Compound of Formula I: L=C$_2$CH$_3$, X=S, Z=H, R$_1$=—CH$_2$CHCH$_2$, R$_2$=CH$_3$ and Rp=H Step 7a. Compound of formula 1.3 of Scheme 1: X=S, R$_1$=—CH$_2$CHCH$_2$, R$_2$=CH$_3$, Rp=C(O)CH$_3$ and Rp$_2$=C(O)CH$_3$;

Into a solution of 2',4"-bis-O-acetyl-6-O-allyl-11-deoxy-10,11-didehydroerythromycin (500 mg, 0.6 mmol), (methylthio)acetic acid (318 mg, 3.0 mmol), and DMAP (146 mg, 1.2 mmol) in CH$_2$Cl$_2$ (4 mL) at room temperature was added dropwise a solution of DIC (378 mg, 3 mmol) in CH$_2$Cl$_2$ (2 mL). The mixture was stirred at room temperature for 12 hours. The crystalline precipitate was removed by filtration. The filtrate was taken up in EtOAc and washed with a saturated aqueous solution of NaHCO$_3$ and with brine, then dried (Na$_2$SO$_4$), filtered and concentrated under reduced pressure. The crude residue was purified on silica gel (hexanes:acetone/49: 1) to provide the title compound (465 mg).

MS (ESI) m/z=928 (M+H)$^+$. $^{13}$C-NMR (125 MHz, CDCl$_3$): δ 170.5, 169.7, 167.4 (2C), 139.8, 136.0, 115.3, 100.2, 96.6, 81.1, 78.5, 72.6, 71.9, 64.6, 63.2, 63.0, 49.4, 45.0, 41.9, 40.6, 35.4, 24.3, 23.4, 21.4, 21.3, 21.0, 20.8, 19.1, 16.2, 13.0, 10.1.

Step 7b. Compound of formula 1.4 of Scheme 1: X=S, R$_1$=CH$_2$CHCH$_2$, R$_2$=CH$_3$, Rp=C(O)CH$_3$ and Rp$_2$=C(O)CH$_3$;

Sodium hydride (20 mg of 60% pure, 0.5 mmol was added to a solution of the compound of Step 7a (100 mg, 0.11 mmol) in DMF (3 mL) at 0° C. The mixture was stirred at 0° C. for 2 hours and quenched by the addition of ice. The resulting aqueous solution was extracted with CH$_2$Cl$_2$. The combined extracts were washed with water, dried (Na$_2$SO$_4$), filtered and concentrated under reduced pressure. The crude residue was purified by flash chromatography (hexanes:acetone/3:2) to give the puretitle compound (76 mg) as an isomeric mixture.

MS (ESI) m/z=928 (M+H)$^+$.

Step 7c. Compound of formula 1.5 of Scheme 1: X=S, R$_1$=—CH$_2$CHCH$_2$, R$_2$=CH$_3$ and Rp=C(O)CH$_3$;

The title compound is obtained from the compound of Step 7b according to the procedure described in Step 1f of Example 1.

Step 7d. Compound of formula 1.6 of Scheme 1: X=S, R$_1$=—CH$_2$CHCH$_2$, R$_2$=CH$_3$ and Rp=C(O)CH$_3$;

The title compound is obtained from the compound of Step 7c according to the procedure described in Step 1h of Example 1.

Step 7e. Compound of formula I: L=CH$_2$CH$_3$, X=S, Z=H, R$_1$=CH$_2$CHCH$_2$, R$_2$=CH$_3$ and Rp=H.

The title compound is obtained from the compound of Step 7d according to the procedure described in Step 2b of Example 2.

Example 8

Compound of formula I: L=CH$_2$CH$_3$, X=S, Z=F, R$_1$=—CH$_2$CHCH$_2$, R$_2$=CH$_3$ and Rp=H Step 8a. Compound of formula I: L=CH$_2$CH$_3$, X=S, Z=F, R$_1$=—CH$_2$CHCH$_2$, R$_2$=CH$_3$ and Rp=C(O)CH$_3$;

The title compound is obtained from the compound of Step 7d according to the procedure described in Step 1i of Example 1.

Step 8b. Compound of formula I: L=CH$_2$CH$_3$, X=S, Z=F, R$_1$=—CH$_2$CHCH$_2$, R$_2$=CH$_3$ and Rp=H.

The title compound is obtained from the compound of Step 8a according to the procedure described in Step 2b of Example 2.

Example 9

Compound of Formula I: L=CH$_2$CH$_3$, X=S, Z=H, R$_1$=—CH$_2$CHCH$_2$-3-quinolyl, R$_2$—CH$_3$ and Rp=H Step 9a. Compound of formula I: L=CH$_2$CH$_3$, X=S, Z=H, R$_1$=—CH$_2$CHCH$_2$-3-quinolyl, R$_2$=CH$_3$ and Rp=C(O)CH$_3$;

Into a degassed solution of the compound of Step 8a (1 equivalent), 3-bromoquinoline (2 equivalents), tri-o-tolylphosphine (0.3 equivalent), and triethylamine (3 equivalents) in acetonitrile, is added palladium (II) acetate (0.15 equivalent). The mixture is heated at 80° C. for 24 hours. The mixture is cooled to room temperature and concentrated under reduced pressure. The crude residue is purified on silica gel column to give the title compound.

Step 9b. Compound of formula I: L=CH$_2$CH$_3$, X=S, Z=H, R$_1$=—CH$_2$CHCH$_2$-3-quinolyl, R$_2$=CH$_3$ and Rp=H.

The title compound is obtained from the compound of Step 9a according to the procedure described in Step 2b of Example 2.

Example 10

Compound of Formula I: L=CH$_2$CH$_3$, X=S, Z=F, R$_1$=—CH$_2$CHCH$_2$-3-quinolyl, R$_2$=CH$_3$ and Rp=H Step 10a. Compound of formula I: L=CH$_2$CH$_3$, X=S, Z=F, R$_1$=—CH$_2$CHCH$_2$-3-quinolyl, R$_2$=CH$_3$ and Rp=C(O)CH$_3$;

The title compound is obtained from the compound of Step 9a according to the procedure described in Step 1i of Example 1.

Step 10b. Compound of formula I: L=CH$_2$CH$_3$, X=S, Z=F, R$_1$=—CH$_2$CHCH$_2$-3-quinolyl, R$_2$=CH$_3$ and Rp=H.

The title compound is obtained from the compound of Step 10a according to the procedure described in Step 2b of Example 2.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula (I)

and the pharmaceutically acceptable salts, esters and prodrugs thereof, wherein

L is selected from the group consisting of:
(1) —CH(OH)CH$_3$;
(2) C$_1$–C$_6$ alkyl, optionally substituted with one or more substituents selected from the group consisting of aryl, substituted aryl, heteroaryl and substituted heteroaryl;
(3) C$_2$–C$_6$ alkenyl, optionally substituted with one or more substituents selected from the group consisting of aryl, substituted aryl, heteroaryl and substituted heteroaryl; and (4) $C_2-C_6$ alkynyl, optionally substituted with one or more substituents selected from the group consisting of aryl, substituted aryl, heteroaryl and substituted heteroaryl;

$R_1$ is selected from the group consisting of $C_1-C_6$-alkyl, $C_2-C_6$-alkenyl and $C_2-C_6$-alkynyl, each optionally substituted with one or more substituents selected from the group consisting of:
(1) halogen;
(2) aryl;
(3) substituted aryl;
(4) heteroaryl;
(5) substituted heteroaryl;
(6) —O—$R_5$, where $R_5$ is selected from the group consisting of:
  a. hydrogen;
  b. aryl;
  c. substituted aryl;
  d. heteroaryl; and
  e. substituted heteroaryl;
(7) —O—$C_1-C_6$-alkyl-$R_5$;
(8) —O—$C_2-C_6$-alkenyl-$R_5$;
(9) —O—$C_2-C_6$-alkynyl-$R_5$; and
(10) —$NR_6R_7$, where $R_6$ and $R_7$ are each independently selected from the group consisting of: hydrogen; $C_1-C_6$-alkyl, optionally substituted with one or more substituents selected from the group consisting of halogen, aryl, substituted aryl, heterocyclic and substituted heterocyclic; $C_2-C_6$-alkenyl, optionally substituted with one or more substituents selected from the group consisting of halogen, aryl, substituted aryl, heterocyclic and substituted heterocyclic; and $C_2-C_6$-alkynyl, optionally substituted with one or more substituents selected from the group consisting of halogen, aryl, substituted aryl, heterocyclic and substituted heterocyclic; or $R_6R_7$ taken together with the nitrogen atom to which they are attached form a 3- to 7-membered ring which may optionally contain one or more hetero functions selected from the group consisting of —O—, —NH—, —N($C_1-C_6$-alkyl)-, —N(aryl)-, —N(heteroaryl)-, —S—, —S(O)— and —S(O)$_2$—;

$R_2$ is selected from the group consisting of:
(1) hydrogen;
(2) $C_1-C_6$-alkyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$, where $R_3$ is selected from the group consisting of:
    i. hydrogen;
    ii. aryl;
    iii. substituted aryl;
    iv. heteroaryl; and
    v. substituted heteroaryl;
  g. —O—$C_1-C_6$-alkyl-$R_3$;
  h. —O—$C_2-C_6$-alkenyl-$R_3$;
  i. —O—$C_2-C_6$-alkynyl-$R_3$; and
  j. —$NR_6R_7$;
(3) $C_2-C_6$-alkenyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$;
  g. —O—$C_1-C_6$-alkyl-$R_3$;
  h. —O—$C_2-C_6$-alkenyl-$R_3$;
  i. —O—$C_2-C_6$-alkynyl-$R_3$; and
  j. —$NR_6R_7$; and
(4) $C_2-C_6$-alkynyl, optionally substituted with one or more substituents selected from the group consisting of:
  a. halogen;
  b. aryl;
  c. substituted aryl;
  d. heterocyclic;
  e. substituted heterocyclic;
  f. —O—$R_3$;
  g. —O—$C_1-C_6$-alkyl-$R_3$;
  h. —O—$C_2-C_6$-alkenyl-$R_3$;
  i. —O—$C_2-C_6$-alkynyl-$R_3$; and
  j. —$NR_6R_7$;

X is O;

Z is selected from the group consisting of:
(1) hydrogen;
(2) halogen; and
(3) methyl; and Rp is hydrogen or a hydroxy protecting group.

2. A compound according to claim 1 wherein L is $CH_2CH_3$, X is —S—, Z is F, $R_1$ is $CH_3$ and $R_2$ and Rp are as defined in claim 1.

3. A pharmaceutical composition comprising a therapeutically effective amount of a compound of claim 1, or a pharmaceutically-acceptable salt, ester or prodrug thereof, in combination with a pharmaceutically acceptable carrier.

4. A method for controlling a bacterial infection in an animal comprising administering to an animal a therapeutically-effective amount of a pharmaceutical composition according to claim 3.

5. A process for preparing a compound represented by the formula

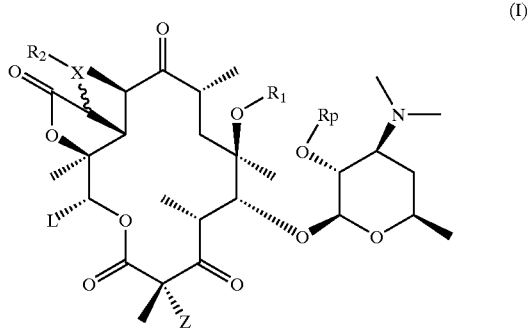

(I)

wherein Z is halogen and L, X, $R_1$, $R_2$, Rp are as defined in claim 1, the method comprising (a) treating a compound represented by the formula

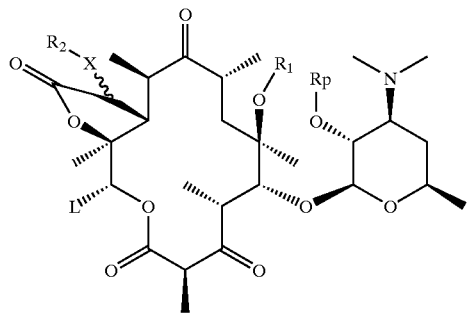

wherein L, X, R₁, and R₂ are as previously defined and Rp is a hydroxy protecting group with a halogenating agent, and optionally deprotecting Rp.

6. The process of claim 5 wherein said halogenating agent is selected from the group consisting of: N-fluorobenzenesulfonimide in the presence of base; 10% $F_2$ in formic acid; 3,5-dichloro-1-fluoropyridinium tetrafluoroborate; 3,5-dichloro-1-fluoropyridinium triflate; $(CF_3SO_2)_2NF$; N-fluoro-N-methyl-p-toluenesulfonamide in the presence of base; N-fluoropyridinium triflate; N-fluoroperfluoro-piperidine in the presence of base; hexachloroethane in the presence of base; $CF_3CF_2CH_{2ICl2}$; $SO_2Cl_2$; $SOCl_2$; $CF_3SO_2Cl$ in the presence of base; $Cl_2$; NaOCl in the presence of acetic acid; $Br_2$/yridine.HBr; $Br_2$/acetic acid; N-bromosuccinimide in the presence of base; LDA/BrCH₂CH₂Br; LDA/CBr₄; and N-Iodosuccinimide in the presence of base; and $I_2$.

7. The process of claim 5 wherein said halogenating agent is N-fluorobenzenesulfonimide in the presence of sodium hydride and the product is a compound represented by formula I wherein Z is F and L, X, R₁ R₂ and Rp are as defined in claim 1.

* * * * *